United States Patent
Gilby (10) Patent No.: US 7,251,026 B2
(45) Date of Patent: Jul. 31, 2007

(54) FLUORESCENCE DETECTOR GEOMETRY

(75) Inventor: Anthony C. Gilby, Foxborough, MA (US)

(73) Assignee: Waters Investments Limited DE (US)

( * ) Notice: Subject to any disclaimer, the term of this patent is extended or adjusted under 35 U.S.C. 154(b) by 316 days.

(21) Appl. No.: 10/650,213

(22) Filed: Aug. 28, 2003

(65) Prior Publication Data

US 2005/0046834 A1 Mar. 3, 2005

Related U.S. Application Data

(63) Continuation of application No. PCT/US02/06336, filed on Mar. 1, 2002.

(60) Provisional application No. 60/273,093, filed on Mar. 2, 2001.

(51) Int. Cl.
*G01N 1/10* (2006.01)

(52) U.S. Cl. ........................ 356/246; 356/317

(58) Field of Classification Search ................ 356/317, 356/246
See application file for complete search history.

(56) References Cited

U.S. PATENT DOCUMENTS

| | | | |
|---|---|---|---|
| 3,704,951 A | 12/1972 | Chupp | |
| 3,715,585 A * | 2/1973 | Harrick | 356/318 |
| 3,734,601 A | 5/1973 | Heiss | |
| 3,807,862 A | 4/1974 | Hatzenbuhler | |
| 4,345,837 A * | 8/1982 | Kallet | 356/317 |
| 4,394,237 A | 7/1983 | Donnelly | |
| 4,988,195 A | 1/1991 | Doyle | |
| 5,194,915 A | 3/1993 | Gilby | |
| 5,327,225 A | 7/1994 | Bender | |
| 5,329,353 A | 7/1994 | Ischimura | |
| 5,444,807 A * | 8/1995 | Liu | 250/458.1 |
| 5,452,723 A | 9/1995 | Wu | |
| 5,780,857 A * | 7/1998 | Harju et al. | 250/458.1 |
| 5,917,606 A | 6/1999 | Kaltenbach | |
| 6,046,807 A | 4/2000 | Chandler | |
| 6,795,177 B2 * | 9/2004 | Doyle | 356/301 |
| 2002/0171827 A1 * | 11/2002 | van den Engh | 356/317 |
| 2003/0202175 A1 * | 10/2003 | van den Engh et al. | 356/138 |
| 2005/0012929 A1 * | 1/2005 | Booker et al. | 356/417 |

FOREIGN PATENT DOCUMENTS

| | | |
|---|---|---|
| JP | 46-009915 | 7/1971 |
| JP | 64-091037 | 4/1989 |
| JP | 7-500191 | 5/1995 |
| JP | 08-159971 | 6/1996 |
| JP | 09-184808 | 7/1997 |
| JP | 10-221244 | 8/1998 |

OTHER PUBLICATIONS

R. Altkorn, et al.; "Low-loss liquid-core optical fiber for low-refractive-index liquids; fabrication, characterization . . . ", Applied Optics/vol. 36, No. 34/Dec. 1, 1997.

(Continued)

*Primary Examiner*—Gregory J. Toatley, Jr.
*Assistant Examiner*—Kara Geisel
(74) *Attorney, Agent, or Firm*—Jamie H. Rose; Anthony J. Janiuk (57) ABSTRACT

Excitation light of a selected wavelength from an excitation monochromator is directed along the long axis of a flow cell containing the sample to be analyzed, generating fluorescence. An emission monochromator is positioned at right angles to the plane of the excitation monochromator and receives the fluorescence from the flow cell utilizing optical components positioned such that the entrance slit of the emission monochromator is aligned with the long axis of the emission window. The intensity of the output from the flow cell is further maximized by positioning a retro-reflecting mirror at the end of the flow channel to effectively double the path-length of the excitation beam, and a reflecting surface on the side of the cell opposite the emission window to increase the collection efficiency and thereby increase the sensitivity of the detector.

15 Claims, 5 Drawing Sheets

OTHER PUBLICATIONS

Fujiwata, et al.; Side-View Type of Waveguide Flow Cells for Fluorimetry as a Detector for Flow Injection Analysis of Lead, Applied Spectroscopy, vol. 46, No. 6, 1992.

Walrafen, et al.; Intensification of Spontaneous Raman Spectra by Use of Liquid Core Optical Fibers, Applied Spectroscopy, vol. 26, No. 6, 1972.

* cited by examiner

FLUORESCENCE DETECTOR GEOMETRY

CROSS REFERENCE TO RELATED APPLICATIONS

This application is a continuation of and claims priority from PCT Application PCT/US02/06336 filed Mar. 1, 2002, which designated the U.S. and claimed priority from U.S. Provisional Application 60/273,093, filed Mar. 2, 2001. The contents of these applications are incorporated herein by reference.

FIELD OF THE INVENTION

The present invention relates to fluorescence detectors, and more particularly to an axially illuminated flow cell having a significantly greater excitation path length per unit volume allowing for improved sensitivity.

BACKGROUND OF THE INVENTION

In the measurement of fluorescence and exitation spectra it is customary to illuminate a sample with monochromatic light from an intense source and to observe the fluorescence emitted by the sample with a monochromator and a photo-electric detection system.

Conventional fluorescence detectors are based on monochromators and an incoherent light source that have essentially the same geometry. Both excitation and emission monochromators lie in the same plane. The cuvette or flow cell is illuminated with excitation light on one side and fluorescence is collected at right angles. The slits of the excitation and emission monochromators are aligned with the long axis of the cell that is perpendicular to the plane of the optics. The cross-section of the cell of conventional detectors in the plane of the optics is typically square.

Standard detection flow cells used in conventional liquid chromatography instruments have the disadvantage that their cell pathways, as a function of their design, are unfortunately short. The width of the emission face of the cell is mapped by collection optics onto the width of the emission monochromator entrance slit. The desired spectral resolution sets a limit to the width of the emission slits, and therefore to the width of the flow cell or cuvette. An exciting beam of light is transmitted through the flow cell to cause fluorescent emission. The amount or intensity of the fluorescent emission is in direct relationship with the path-length of the exciting beam within the sample. As sample volumes are reduced the resulting path-length is proportionally decreased causing diminished sensitivity of the detector.

Fluorescence measuring apparatus of the foregoing type exhibit certain disadvantages. One of the more significant problems is the comparatively low magnitude of the output signal due to the limits encountered by the relatively short path-length. In the usual form of apparatus, light from an intensely bright light source such as a high pressure Xenon arc is focused on the entrance slit of the excitation monochromator, and an image of the exit slit is focused on a sample by means of a first optical system. Fluorescence from the sample is collected by a second optical system and focused on the entrance slit of an emission monochromator such that the signal at the exit slit of the emission monchromator is directed to a detector. A sensitive detector such as a photomultiplier is placed after the emission monochromator exit slit to measure the fluorescent signal at the selected wavelength. Unfortunately, this conventional method of fluorescent sample detection is degraded as the size of the sample is reduced.

In light of this significant detection limitation, caused by a short excitation path-length, there have been a number of attempts employed in the prior art to increase excitation path-lengths, and hence the sensitivity of the analysis.

Work has been done in Raman and fluorescence detection using light guiding flow cells with axial illumination in order to increase the absorbing path-length. In this approach lasers are used for excitation and emission that is collected axially, either in the forward or back-scattered direction. These cells are made from capillary tubing where the analyte solution refractive index exceeds that of the tube walls and the excitation light is guided by total internal reflection. However, in spite of their apparent demonstrated advantages, they currently receive little use because silica-based glasses have high refractive indices (n>1.46). The requirement for total internal reflection dictates that the refractive index of the core sample liquid exceed that of the capillary wall, which severely limits utility.

Hollow glass or silica waveguides used with low-refractive index liquids have drawbacks from an optical point of view. Since they function through internal reflection at the external surface of the glass tube they allow light to propagate through the tubing wall as well as the liquid core. From a spectroscopic point of view, propagation in the glass wall has several adverse consequences. Propagation through the glass reduces the path-length of light in the liquid. Also, particularly in Raman studies, propagation in the glass wall results in the generation of silica bands, contributing to unwanted background noise.

The substitution of Telfon AF tubing with a refractive index less than water overcomes some of these difficulties. In these light guiding cells, excitation path length is increased. However, the emitted fluorescence must travel the length of the light guiding section of the sample liquid and may be subject to re-absorption unless the solutions are extremely dilute. Self absorption can severely limit the linear dynamic range of sample concentration in a light guiding cell.

SUMMARY OF THE INVENTION

The photometric flow cell according to the invention provides more light absorption by the sample due to an increased path-length of the excitation beam. Increased excitation path-length allows a sample to produce more fluorescent photons causing the fluorescence detector to have greater detection sensitivity. As a consequence of the flow cell design, the path length traversed by the emitted photons is small, avoiding non-linearity associated with self absorption.

According to the invention, a photometric apparatus for small sample volumes is comprised of a cell body. The cell body has light input optics arranged adjacent to the surface of the cell body. A light source is presented, generally a high-radiance portion of a high-pressure Xenon arc, and a monochromator selects light of a predetermined wavelength or wavelength range through the light input optics. The light input optics are comprised of very low aberration optics, so that the small, high-radiance portion of the high-pressure Xe arc is focused, after wavelength selection, onto the small end cross-section of the flow cell, thus providing axial illumination of the flow channel with increased path-length.

The axial illumination of the flow cell causes the sample to produce greater fluorescence that is emitted in all directions. More fluorescence is collected from the long side of the flow cell by the placement of a mirror surface opposite the emission window that directs errant fluorescent emission through the emission window. Additional sensitivity is achieved within the inventive flow cell by the retro-reflection of the excitation beam off the curved end mirror surface to cause the beam to double-pass the flow channel, thereby significantly increasing the path-length. Minimum volume at this extended path-length is accomplished by utilizing the referenced low aberration optics designed for the source collection and excitation monochromator, so that the small, high-radiance portion of the high-pressure Xenon arc is focused axially onto the small end cross-section of the flow cell. The axial illumination of the flow cell is achieved by having the plane of the excitation optics horizontal, resulting in the long axis of the flow cell being horizontal and the plane of the emission optics being vertical.

This change in the geometry of the optics on two separate planes allows for improved sensitivity in photo-detection by allowing an increased path-length by the axial illumination of the flow cell and the collection of the resulting emission from the long slit-shaped side of the flow cell, parallel to the axis of the flow cell.

Advantages of the present invention include the significantly increased path-length through the flow cell resulting in greater intensity of the output signal. This advantage allows greater sensitivity for small samples compared with conventional sized flow cells. A further benefit of the present invention is the simplicity of measuring the signal because of the lack of pre-filter and post-filter effects of solvents.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

The flow cell according to the invention is used for analyzing small sample volumes typically between 0.5 to 15 µL. Generally, the analysis of these small sample volumes is accomplished with the use of an axially excited flow cell having a retro-reflective mirror that allows for an increased pathlength through the sample. The use of this inventive flow cell with excitation optics and emission optics on different planes allows for a significantly greater pathlength through a sample of interest and therefore greater sensitivity in the detector results.

Figure 1A:
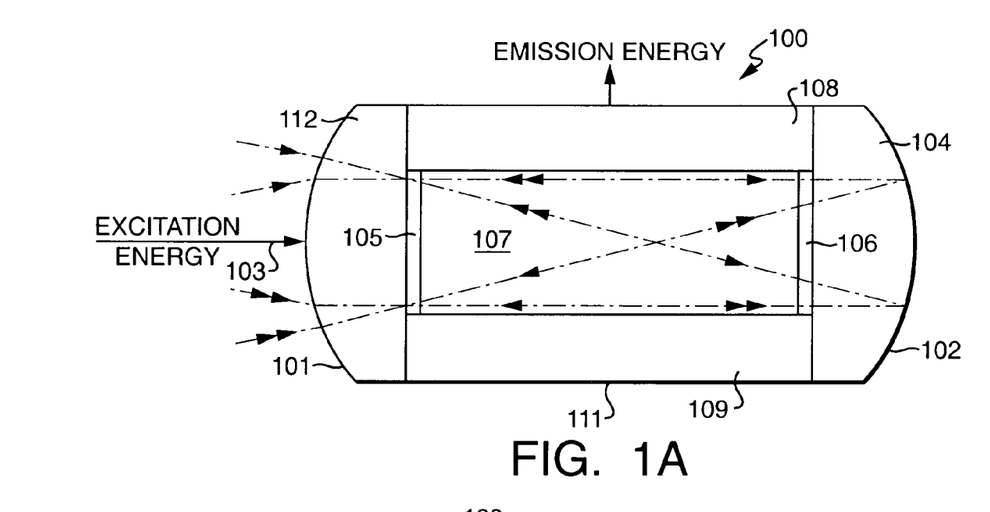
FIG. 1A illustrates a side view of a flow cell according to the invention.
Figure 1B:
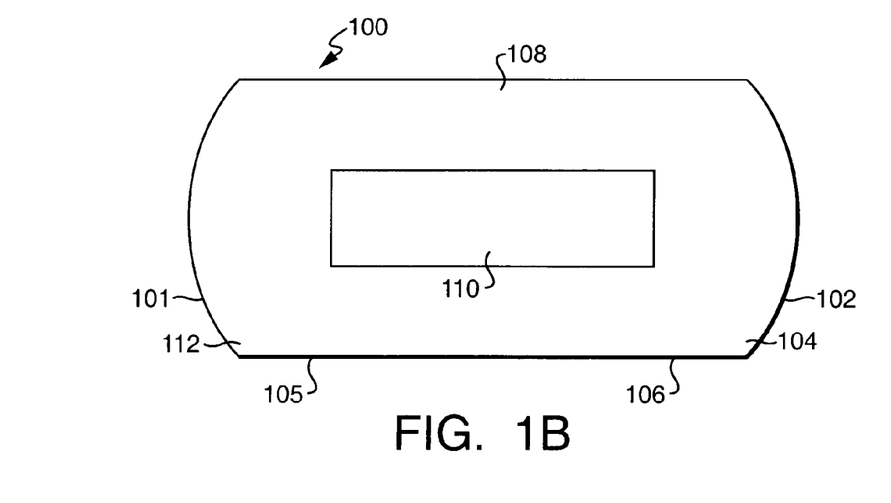
FIG. 1B illustrates a top view of a flow cell according to the invention.
Figure 2A:
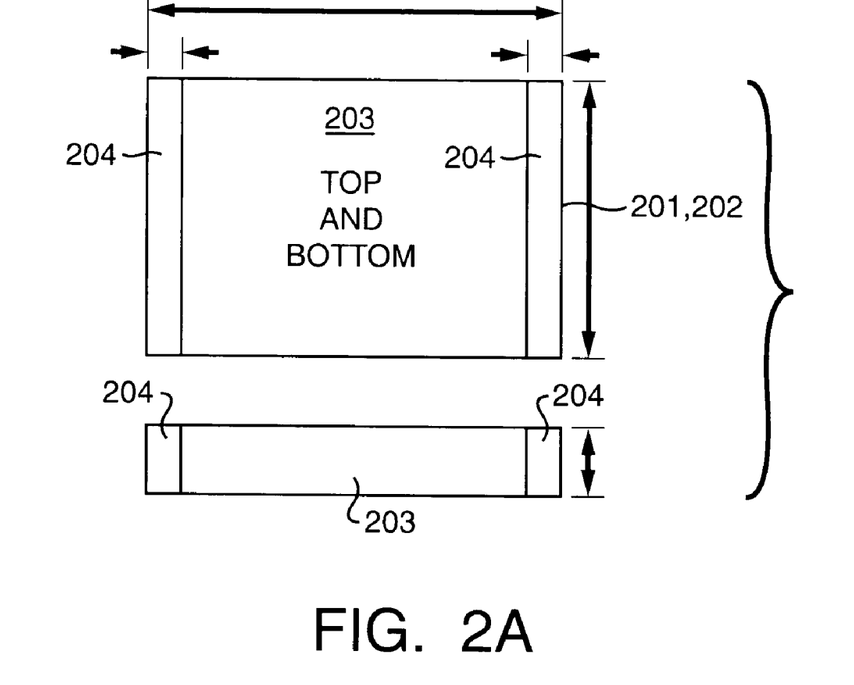
FIGS. 2A, 2B, 2C and 2D, illustrate components used in the construction of one embodiment of the inventive flow cell.
Figure 2B:
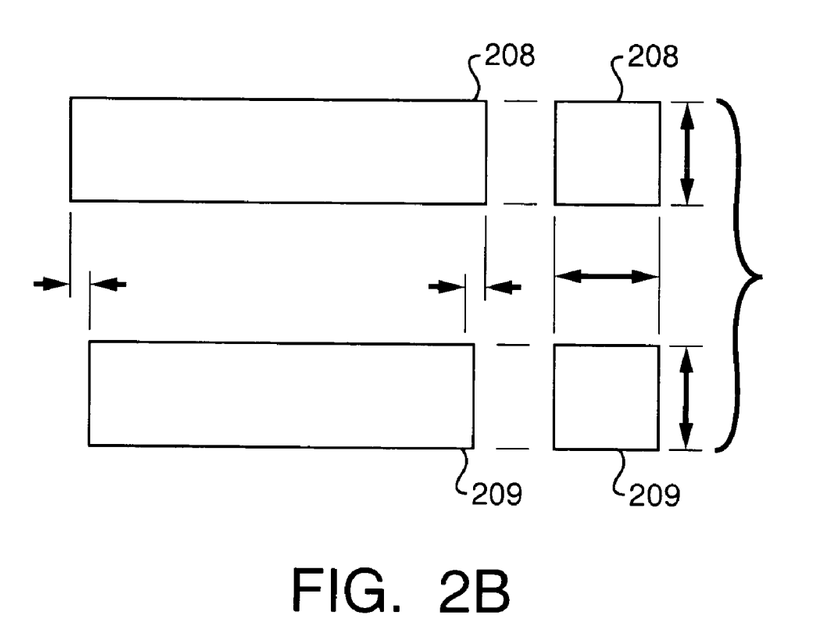
Figure 2C:
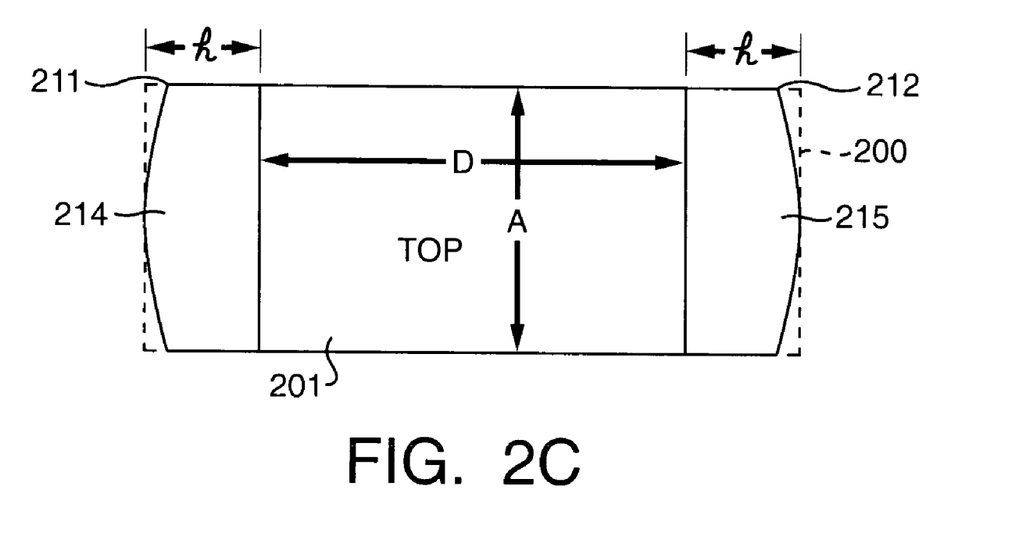
Figure 2D:
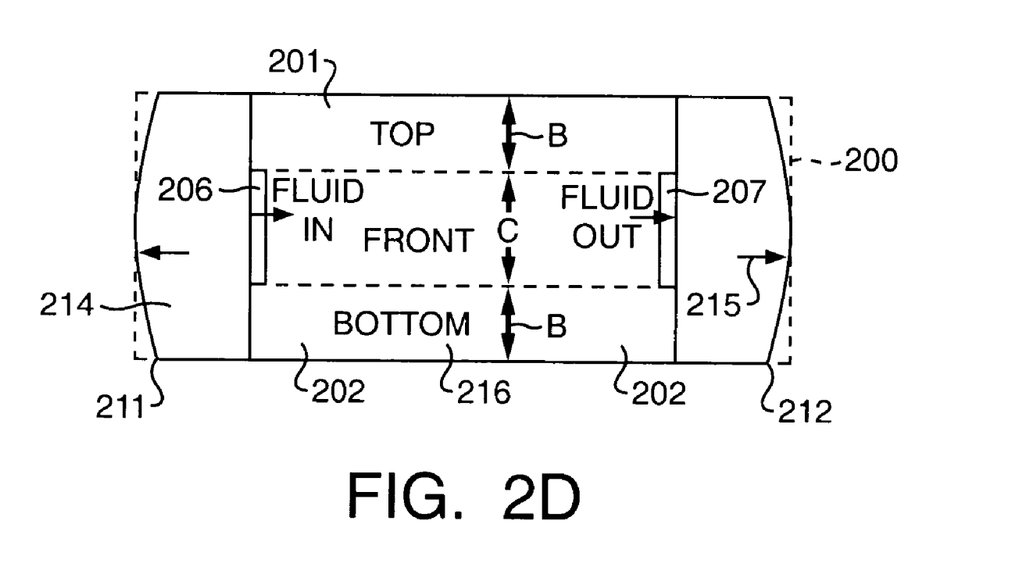

Referring to FIGS. 1A and 1B, the flow cell 100 according to the invention is constructed from a combination of black quartz and clear non-fluorescence quartz. The clear quartz is UV grade having a low fluorescence, such as Suprasil or an equivalent clear quartz known to those skilled in the art. The flow cell 100 has a proximal end 101 and a distal end 102. The proximal end 101 contains an excitation lens 112 that allows an excitation beam 103 to travel into a flow channel 107. The distal end 102 contains a retro-reflecting mirrored lens 104. The retro-reflecting mirrored lens 104 is positioned at the distal end 102 of the flow cell 100 opposite the end that receives the excitation beam 103.

The excitation beam 103 enters the flow channel 107 at the proximal end 101 of the flow cell 100 and travels axially through the flow channel 107. The excitation beam 103 is then redirected through the flow channel 107 by the use of the retro-reflecting mirrored lens 104 at the distal end of the flow cell 100. The retro-reflecting mirrored lens 104 is formed by coating the exterior of an optical lens with evaporated aluminum with a $SiO_2$ overcoat forming the retro-reflecting mirror 104. The retro-reflecting mirrored lens 104, positioned at the distal end 102 of the flow cell 100, redirects the excitation beam 103 back through the sample of interest allowing the excitation beam 103 to travel through the sample at least twice. The double pass of the excitation beam 103 through the sample within the flow channel 107 effectively doubles the path-length of the excitation beam 103 through the sample thereby increasing the fluorescence of the sample and thus further improving the sensitivity of the detector.

The flow cell 100 according to the invention has an inlet port 105 and an outlet port 106 that are located on opposite ends of the flow channel 107 that allow a sample to pass through the flow cell 100 in order to undergo analysis. The flow channel 107 is formed from a top plate 108 and a bottom plate 109 with the flow channel 107 positioned between the two opposing plates 108, 109. The top plate 108 is constructed with black quartz and clear quartz forming an emission window 110. The bottom plate 109 is also constructed with black quartz and clear quartz. The clear quartz area of the bottom plate 109 is coated with evaporated aluminum with a $SiO_2$ overcoat providing a reflective mirrored surface 111 to the bottom plate 109. The mirrored surface 111 of the bottom plate 109 causes emission energy to be directed through and out the emissions window 110 contained within the top plate 108.

Referring to FIGS. 2A, 2B, 2C and 2D, an illustrative flow cell and a method of constructing the inventive flow cells is shown. The inventive flow cell 200 is constructed using a series of plates having specific dimensions (as a function of the desired size of the flow cell), that when assembled produce a flow cell having a reduced volume and an increased path-length. The flow cell 200 has a top plate 201 and a bottom plate 202 that are substantially identical in size and rectangular in configuration. In this illustrative embodiment, both plates 201 and 202 are approximately 4 mm by 6 mm and have a center area 203 approximately 4 mm wide by approximately 5 mm long that is made of clear quartz that is UV grade having a low fluorescence. The center area 203 of both plates has at each end a band 204 of black quartz that is approximately 0.5 mm wide.

The bands of black quartz 204 at the ends of the top and bottom plates 201 and 202 forming the flow cell block excitation light from entering the end cross-section of the clear quartz plates within the center area 203, which form the top and bottom of the flow cell 200. These bands of black quartz 204 both reduce scattered light and define a flow cell 200 entrance aperture, which controls the spectral bandwidth of light entering the flow cell 200. These same bands of black quartz 204, particularly at the ends of the top plate 201, prevent the emission collecting optics from seeing the internal end surfaces of the flow cell 200, minimizing the collection of scattered excitation light.

Both plates 201, 202 are approximately 1.0 to 1.55 mm thick depending on the volume within the flow cell 200. The bottom plate 202 is coated with evaporated aluminum with a $SiO_2$ overcoat on the exterior of the bottom plate 202. The evaporated aluminum coating forms a mirrored surface 216 within the center area 203 of the bottom plate 202. The top plate 201 is left uncoated allowing the center area 203 of the top plate 201 to form an emissions window.

Positioned between the top plate 201 and the bottom plate 202 are two smaller middle plates that when positioned form a flow channel 205 (not shown) having an inlet port 206 and an outlet port 207. A rear middle plate 208 is configured from black quartz. The rear middle plate 208 has a length that is equal to the length of the top plate 201 and bottom plate 202. In a first illustrative embodiment the rear middle plate 208 is approximately 1.5 mm thick and approximately 1.5 mm wide. A front middle plate 209 is configured from black quartz and within the first illustrative embodiment is approximately 1.5 mm thick and approximately 1.5 mm wide. The front middle plate 209 has a length that approximately 0.4 mm shorter than the rear middle plate 208. The front middle plate 209 is positioned within the flow cell assembly in the center of the top plate 201 and bottom plate 202. The centering of the front middle plate 209 forms a gap of approximately 0.2 mm on either side of the front middle plate 209. These gaps form the inlet port 206 and the outlet port 207. It is contemplated within the scope of the invention that the inlet port 206 and the outlet port 207 can be formed by boring or otherwise fabricating holes into a front middle plate 209 having the same length of the top and bottom plates.

The combination of the width of the rear middle plate 208 and the front middle plate 209 and the thickness of these two plates 208, 209 in the first illustrative embodiment form a flow channel 205 having an approximate dimension of 1.0 mm wide by 1.5 mm high by 6.0 mm long in this embodiment. These dimensions produce a flow channel having a volume of approximately 9.0 μL.

In a second illustrative embodiment the height of the rear middle plate 208 and the front middle plate 209 are decreased to approximately 0.4 mm. The width of the rear middle plate 208 and the front middle plate 209 are increased to approximately 1.8 mm. The length of the top and bottom plates 201, 202 remains the same. The changed dimensions of the middle plates 208, 208, in the second illustrative embodiment, result in the flow channel 205 having an approximate dimension of 0.4 mm wide by 0.4 mm high by 6.0 mm long. The dimension of the flow channel 205 within the second illustrative embodiment produces a low volume flow channel 205 having a volume of approximately 0.96 μL. In this second illustrative embodiment the thickness of the top plate 201 and bottom plate 202 are increased to approximately 1.55 mm in order to make the external dimensions of the two embodiments the same, facilitating interchangeability in a common cell mount. The flow channels 205 of both illustrative embodiments are configured to withstand internal pressure of up to approximately 500 psi.

The combined plates forming the flow cell 200 have a first end 211 and a second end 212. In both illustrative embodiments affixed to each end 211, 212 of the combined plates are optical lenses. An excitation lens 214 is affixed to the first end of the combined plates that allows the flow channel 205 to receive an excitation beam. A second optical lens 215 is affixed to second end of the combined plates. The second optical lens 215 is coated on its exterior surface with evaporated aluminum with a $SiO_2$ overcoat. The aluminum coating of this second optical lens 215 causes it to have a mirrored surface. This mirrored surface at the end of the flow channel 205 opposite the excitation lens 214 allows the excitation beam to be retro-reflected back through the flow channel 205.

The curvature of spherical/plano excitation lens 214 is chosen so that a pupil of the excitation optical system is formed in the vicinity of the retro-mirrored second optical lens 215. The curvature of the coated lens forming retro-mirror second optical lens 215 is chosen so that the entrance aperture of the cell is imaged back on itself with unit magnification. Thus reflection of excitation light from the cell internal walls is minimized, which minimizes the stray light background in the emission monochromator.

Before the various plates and parts shown above are fused together, the parts are machined and polished to a roughness allowing for liquid gasket seal and low scatter optical transmission and reflection where appropriate. The parts may also be affixed to each other by the use of a variety of adhesives and methods known to those skilled in the art.

Figure 3:
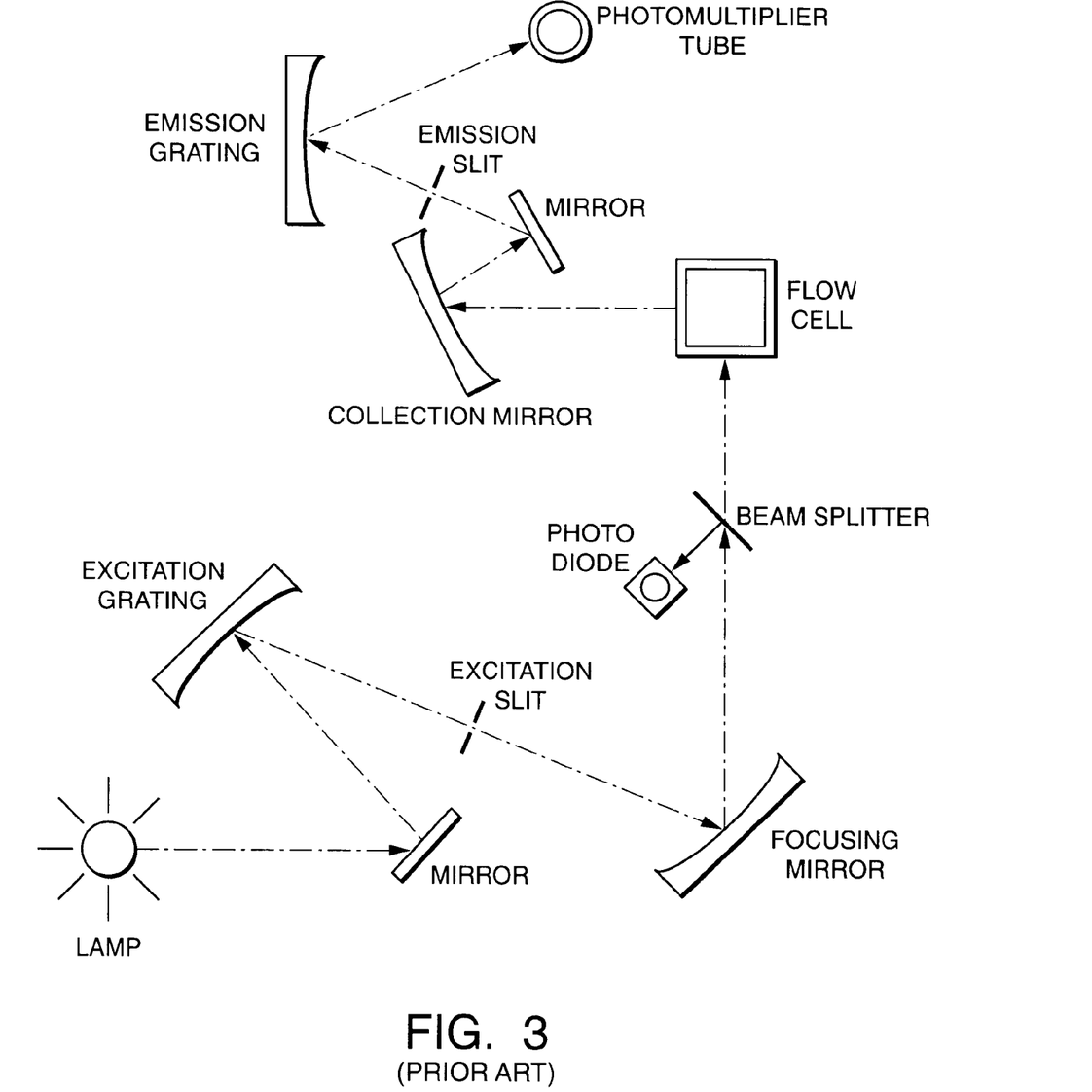
FIG. 3 shows prior art optics all in one plane.

Referring to FIG. 3, the prior art optics are shown for a typical detector. Both the excitation optics and the emission optics are on the same plane. The excitation beam is passed through the flow cell and the resulting emissions are collected at right angles. The pathlength through the sample is limited and determined by the width of the flow cell.

Figure 4A:
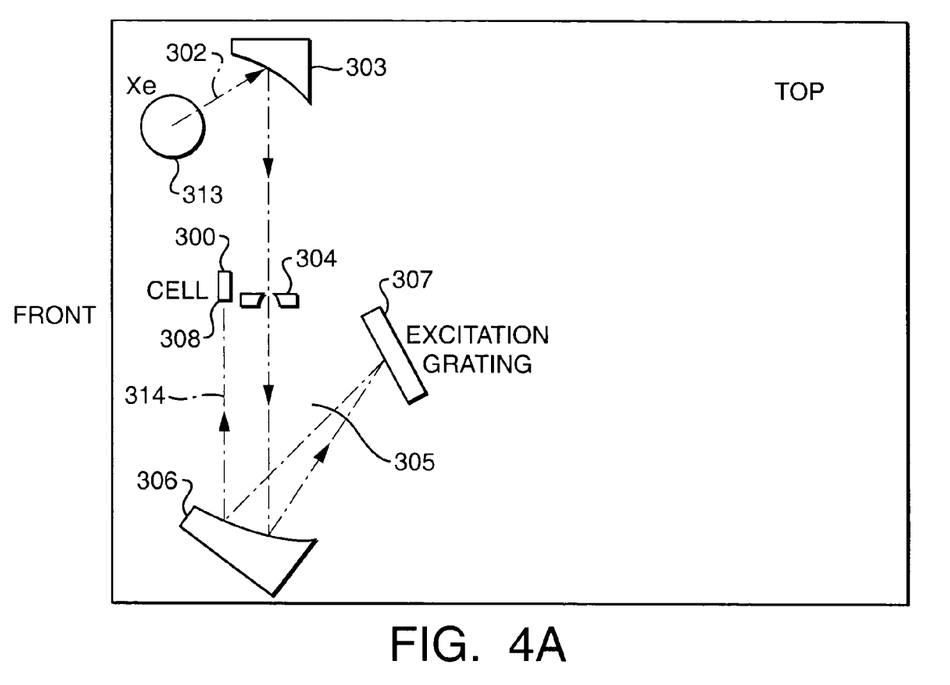
FIG. 4A illustrates the excitation optics of the present invention, on a horizontal plane.
Figure 4B:
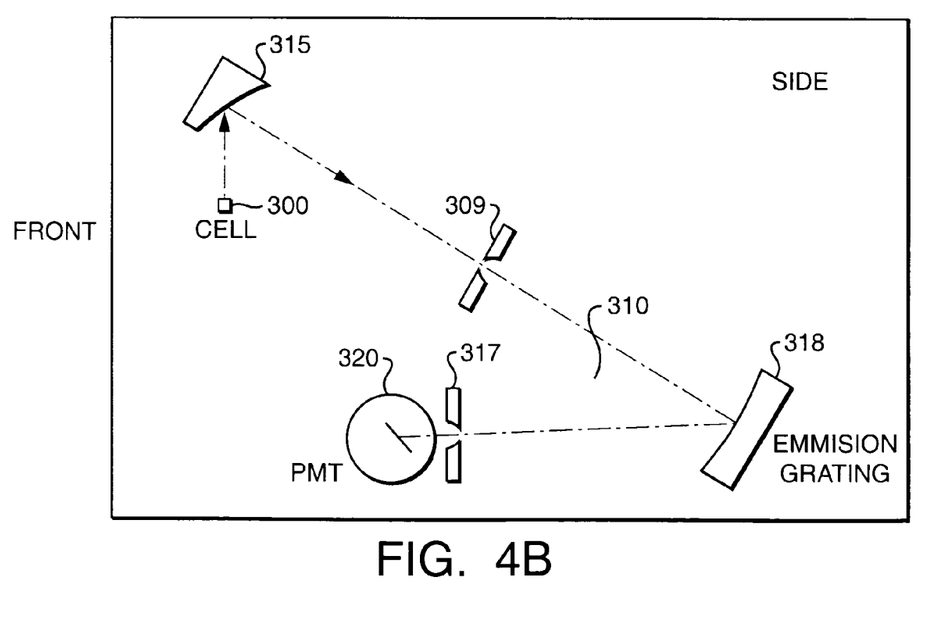
FIG. 4B illustrates the emission optics of the present invention, on a vertical plane aligned with the long axis of the flow cell.

The optics according to the invention exist on two separate planes. FIGS. 4A and 4B provide a schematic representation of emission and excitation optics on two separate planes as used within the inventive flow cell. The optics are designed to be very low aberration optics. A light beam 302 produced from a Xenon arc 313 is directed to collection optics 303 that further directs the light beam 302 toward an entrance slit 304 of an excitation monochromator 305. The light beam 302 entering the entrance slit 304 is directed toward excitation optics 306 to an excitation grating 307. The light beam 302 is then redirected from the excitation grating 307 back to the excitation optics 306. The excitation optics are very low aberration optics designed for source collection, so that the small high-radiance portion of the light beam 302, which in the illustrative embodiment is generated from a Xenon arc 313, produces an excitation beam 314 that is focused axially onto a small end cross-section 308 of the inventive flow cell 300.

The small end cross section 308 of the flow cell 300 containing an excitation lens is roughly square. The flow cell 300 containing the liquid sample of interest receives the excitation beam 314 and the sample is excited by the axial flow of the excitation beam 314 through the sample that is then retro-reflected back through the sample by a mirrored lens at the end of the flow channel. The passing of the excitation beam 314 back and forth through the sample along the long axis of the flow cell produces greater fluorescence than that of conventional flow cells. The resulting fluorescence from the sample is emitted in all directions. The inventive flow cell 300 is mirrored on the side of the flow cell 300 opposite the emission window to collect fluorescence which is headed in the wrong direction.

The fluorescence emitted from the flow cell 300 is collected from the emission window on the long side of the flow cell 300 and is directed toward emission optics 315 that directs the fluorescence toward an emission entrance slit 309 of an emission monochromator 310. The emission slit 309 is aligned with the long axis of the flow cell emission window.

It is this fact that causes the emission optics to lie in a plane at right angles to the excitation optics. The fluorescence then passes through the emission entrance slit 309 to an emission grating 318. Both the plane of the excitation monochromator 305 and, the long axis of the flow cell 300 are horizontal. The plane of the emission optics 315 and the emission monochromator 310 are perpendicular to the excitation monochromator 305 and the long axis of the flow cell 300.

Referring specifically to FIG. 4b, there is shown a schematic representation of the emission monochromator 310. The fluorescence emitted from the flow cell 300 is received by the vertically positioned emission monochromator 310. The vertical position of the emission monochromator 310 allows the excitation beam 314 to travel axially through the flow cell 300. The axial direction of the excitation beam 314 through the flow cell 300 increases the path-length significantly over prior devices whose plane of optics is all horizontal as shown in FIG. 3. The collected emission light passes through the entrance slit 309 and is directed upon the emission grating 318. The fluorescence is directed by the emission grating 308 and focused through an exit slit 317 of the emission monochromator 308. The fluorescence emerging from the exit slit 317 comprises a selected, monochromatic portion of the luminescent emission from the sample. The emerging luminescence is received by a photomultiplier tube 320, which is of conventional construction known in the art and preferably is of a type, which exhibits sensitivity at the particular wavelengths of interest. The photomultiplier tube 320 produces a signal that is relative to the intensity of the fluorescence emitting from the exit slit 317.

Although the source of visable light described in the illustrative embodiment herein is a Xenon arc it should be appreciated that other suitable sources of visible or invisible light that are know in the art can be used, such as a Xenon/Mercury arc, Deuterium arc, Tungsten Halogen lamp or the like.

Although the dimension of the flow channel of the illustrative embodiment herein produces a volume of sample of between 0.96 μL and 9.0 μL it should be appreciated that by changing the dimension of the middle plates during construction of the flow cell volumes that are significantly greater or smaller can be achieved.

Although the illustrative embodiment shows a retro-reflecting mirror at the end of the flow channel it should be appreciated by one skilled in the art that the axial illumination of the flow cell itself produces a greater pathlength and thus a detector with greater sensitivity. Likewise, it should be appreciated that the retro reflective mirror at the end of the flow channel can be configured to reflect the excitation beam back and forth multiple times thus greatly increasing the pathlength of the excitation beam and therefore the sensitivity of the detector.

Additionally, it should be appreciated that while an aluminum retro-reflecting surface is described as deposited on the outside of the end of the flow cell, other materials can be used to effect retro-reflection, such as silver, gold or the like, depending on the excitation wavelengths to be used. It will also be appreciated that a concave internal surface can be used as the retro-mirror surface, coated with an appropriate reflective material.

Various other changes, omissions and additions in the form and detail of the present invention may be made therein without departing from the spirit and scope of the invention. Therefore, the above description should not be construed as limiting, but merely as exemplification of the various embodiments.

What is claimed:

1. A flow cell for photometric analysis comprising:
    a flow channel having a proximal end and a distal end;
    an inlet channel and an outlet channel in fluid communication with said flow channel;
    an excitation lens positioned within the proximal end of said flow channel;
    a retro-reflecting mirrored lens positioned at the distal end of said flow channel;
    an emissions window positioned substantially parallel to the long axis of said flow channel; and
    a reflective surface positioned opposite said emissions window.

2. The flow cell of claim 1 wherein said excitation lens allows for an excitation beam to travel axially through said flow channel.

3. The flow cell of claim 2 wherein said retro-reflecting mirrored lens reflects said excitation beam back through said flow channel.

4. The flow cell of claim 2 wherein said retro-reflecting mirrored lens reflects said excitation beam back through said flow channel multiple times.

5. The flow cell of claim 4 wherein said reflective surface opposite said emission window directs additional fluorescence out said emission window.

6. The flow cell of claim 1 wherein said flow channel has a volume of between 0.5 and 15 μL.

7. The flow cell of claim 6 wherein said flow channel has a volume of between 8 and 9.5 μL.

8. The flow cell of claim 6 wherein said flow channel has a volume of between 0.75 and 1.25 μL.

9. The flow cell of claim 2 wherein said excitation beam is delivered to said flow channel from an excitation monchromator having optics in a first plane.

10. The flow cell of claim 5 wherein said fluorescence is delivered to an emission monchromator having optics in a second plane perpendicular to said first plane.

11. A method of constructing a flow cell, comprising:
    forming plates of various dimensions of clear quartz and black quartz;
    assembling said plates, wherein said various dimensions form a flow channel having an inlet port and an outlet port;
    fusing said plates to each other; and
    fusing lenses to both ends of assembled plates.

12. A flow cell for photometric analysis comprising:
    a cell body;
    a flow channel formed in said body having an input means and an output means;
    a light input means positioned axially to said cell body where said light input means and said cell body are within a first plane;
    a light source means for emitting an excitation beam of a predetermined wavelength, wherein said excitation beam flows axially through said flow channel producing fluorescence;
    a means for retro-reflecting said excitation beam back through said flow channel, comprising a mirrored optical lens positioned within said flow channel opposite said light input means;
    a light output means positioned substantially parallel to a long axis of the flow channel and to said first plane of said cell body;
    a means for reflecting said fluorescence toward said light output means; and
    a light detector means positioned contiguous to said light output means.

13. A flow cell for photometric analysis comprising:

a cell body comprising plates of various dimensions being formed from clear quartz and black quartz;

a flow channel formed in said body having an input means and an output means;

a light input means positioned axially to said cell body where said light input means and said cell body are within a first plane;

a light source means for emitting an excitation beam of a predetermined wavelength, wherein said excitation beam flows axially through said flow channel producing fluorescence;

a means for retro-reflecting said excitation beam back through said flow channel;

a light output means positioned substantially parallel to a long axis of the flow channel and to said first plane of said cell body;

a means for reflecting said fluorescence toward said light output means; and a light detector means positioned contiguous to said light output means.

14. A flow cell for photometric analysis comprising:

a cell body;

a flow channel formed in said body having an input means and an output means;

a light input means positioned axially to said cell body where said light input means and said cell body are within a first plane;

a light source means for emitting an excitation beam of a predetermined wavelength, wherein said excitation beam flows axially through said flow channel producing fluorescence;

a means for retro-reflecting said excitation beam back through said flow channel, comprising coating the back of an optical lens with evaporated metal chosen from the set consisting of aluminum, silver, and gold;

a light output means positioned substantially parallel to a long axis of the flow channel and to said first plane of said cell body;

a means for reflecting said fluorescence toward said light output means; and a light detector means positioned contiguous to said light output means.

15. The flow cell according to claim 14 wherein said evaporated metal is aluminum.

\* \* \* \* \*